United States Patent
Hassler et al.

[11] Patent Number: 6,090,145
[45] Date of Patent: Jul. 18, 2000

[54] PARTIAL SCAPHOID IMPLANT AND METHOD OF TREATING AILMENTS OF THE SCAPHOID

[75] Inventors: Michel Hassler, Saint Ismier; Jean-Pierre Pequignot, Nice, both of France

[73] Assignee: Societe Industrielle de Combustible Nucleaire S I C N, France

[21] Appl. No.: 08/988,496

[22] Filed: Dec. 10, 1997

[51] Int. Cl.[7] .................................................. A61F 2/42
[52] U.S. Cl. .............................................. 623/21; 623/18
[58] Field of Search ............................. 623/21, 18, 16; 606/62, 69, 70, 71, 74

[56] References Cited

U.S. PATENT DOCUMENTS

| | | | |
|---|---|---|---|
| 3,526,005 | 9/1970 | Bokros et al. | 623/21 |
| 4,005,163 | 1/1977 | Bokros | 264/81 |
| 4,164,793 | 8/1979 | Swanson | 128/92 |
| 4,166,292 | 9/1979 | Bokros | 128/92 |
| 4,198,712 | 4/1980 | Swanson | 128/92 |
| 4,936,860 | 6/1990 | Swanson | 623/21 |
| 4,955,915 | 9/1990 | Swanson | 623/21 |
| 5,326,364 | 7/1994 | Clift, Jr. et al. | 623/21 |
| 5,743,918 | 4/1998 | Calandruccio et al. | 623/21 |
| 5,780,119 | 7/1998 | Dearnaley et al. | 427/528 |
| 5,782,926 | 7/1998 | Lamprecht | 623/21 |

OTHER PUBLICATIONS

High–strength high–surface–area, Porus carbon made from submicron–diameter carbon filaments, Cabon, vol. 34, Issue 9, 1996 pp. 1162, 1996.

Commercial brochure entitled "Scaphoid Partial Implant: An Alternative to Arthrodesis" present at a Paris trade fair on Dec. 12, 1996.

J.P. Pequignot et al., "Partial Prosthesis of the Scaphoid from Silastic to Pyrocarbon", Fourth Congress of F.E.S.S.H., Bologna, Italy, Jun. 1997.

*Primary Examiner*—David H. Willse
*Assistant Examiner*—Suzette J. Jackson
*Attorney, Agent, or Firm*—Ostrolenk, Faber, Gerb & Soffen, LLP

[57] ABSTRACT

A prosthesis for treating ailments of the scaphoid consists of an implant shaped and sized to serve as a partial replacement of the scaphoid. The prosthesis consists of an element made of a material whose Young's modulus is approximately in the range 10–35 GPa, such as pyrolytic carbon, and having an external surface with a first curved portion having a small radius of curvature corresponding to the conjugated profile of the scaphoid between the head of the capitate and the radius, and a second curved portion having a large radius of curvature corresponding to the profile of the scaphoid facing the radius. Preferably, the partial scaphoid implant is elliptical in each of three mutually perpendicular planes. A method for treating ailments of the scaphoid consists in the surgical removal of a proximal portion of the scaphoid, while leaving the distal fragment thereof in place, and replacing the removed fragment by a prosthesis as described above.

21 Claims, 5 Drawing Sheets

PARTIAL SCAPHOID IMPLANT AND METHOD OF TREATING AILMENTS OF THE SCAPHOID

BACKGROUND OF THE INVENTION

The present invention relates to the field of prostheses and, more particularly, to a prosthesis and a method for treating ailments of the scaphoid (os scaphoideum).

The scaphoid is one of the eight or nine principal bones forming part of the wrist in humans. The wrist is a very complicated joint since it consists, not of two bones rubbing against one another, but of eight or nine principal bones of unusual shapes held and moving in equilibrium under control of a highly developed system of ligaments. The scaphoid is of particular importance clinically because it is the wrist bone which tends most often to be fractured.

The scaphoid is the largest of the bones located in the first row of wrist bones (known as the first carpal row or proximal carpal row). The other principal bones in the proximal carpal row are the lunate, triangular and pisiform bones. The bones of the proximal row are articulated to the radius (of the forearm) and the articular disk. The second carpal row (also known as distal row) contains the trapezium or greater multangular, the trapezoid or lesser multangular, the capitate and the hamate. The bones of this second carpal row are firmly attached to the metacarpal bones of the hand.

The scaphoid is surrounded by the trapezium, trapezoid, capitate, lunate and radius, as illustrated in FIG. 1 (which illustrates the bone of the right hand viewed looking towards the palm). The scaphoid is "articulated" at the proximal side with the radius and the distal side with the trapezium and trapezoid. Fractures of the scaphoid tend to occur, in around 70% of cases, in the central third thereof, as illustrated by the shaded area F in FIG. 1. If the fracture is not properly treated then a pseudathrosis or necrosis of the proximal bone fragment can occur. This is because, in a third of cases, blood supply to the scaphoid is furnished only by vessels at the distal side. Other ailments too, besides fractures, can lead to damage to or degeneration of the scaphoid.

It could be contemplated to treat ailments of the scaphoid by implanting a prosthesis into the wrist of a patient. However, in order for such a technique to be successful, the prosthesis in question must allow the patient to retain or regain mobility of the wrist joint. Further, the prosthesis must be stable, that is, the prosthesis and the bones of the wrist must correctly return to their original positions after a movement has been terminated, without dislocation. Other important considerations are the comfort of the implant for the patient, at rest and during different types of movement and the biocompatibility and durability of the prosthesis.

It is not straightforward to determine the appropriate combination of shape, size and material enabling a suitable prosthesis to be produced for use in treating ailments of the scaphoid. For example, the present inventor has found that there are disadvantages involved in the use of certain of the materials which might have been contemplated, notably polyethylene, ceramic zircon and titanium.

In the case of polyethylene, the prosthesis is too soft, i.e. its modulus of elasticity, also called Young's modulus, which is of the order of 1 GPa (Giga Pascal), is far too low compared with that of bone, the latter being comprised within the range of 15 to 25 GPa. Such a prosthesis is therefore subject to deformation and becomes crushed after a relatively short period of use. Wear debris resulting from deterioration of the prosthesis can then migrate in some areas of the patient's wrist, which can cause painful inflammatory reactions for the patient.

In the case of zircon titanium, the prosthesis is too hard. Indeed, the respective Young moduli of zircon and titanium are respectively about 300 and 110 GPa, which is far too high with respect to the Young's modulus of bone. The prosthesis does not deform enough upon motions of the wrist, causing the bones in contact with the prosthesis to be stressed by the latter. Because of bad distribution of stresses, the patient experiences discomfort, for example, when pressing a fist down onto a surface. Also, there is a significant risk of wearing out the cartilage or bony surfaces in contact with the prosthesis due to the hardness of the prosthesis material.

OBJECTS AND SUMMARY OF THE INVENTION

It is an object of the present invention to provide an implant or prosthesis for use in treatment of ailments of the scaphoid which resists wear and does not wear out the bones of the wrist in contact with the prosthesis.

It is a further object of the present invention to provide such an implant or prosthesis which is adapted to maintain mobility of the wrist, and which is stable kinematically (that is, which ensures that after a movement of the wrist joint the implant returns reliably to its initial position) and physically (that is, it resists wear and is biocompatible).

It is a further object of the present invention to provide a method of treating ailments of the scaphoid whereby to maintain mobility and stability of the wrist joint.

BRIEF SUMMARY OF THE INVENTION

According to one aspect thereof, the present invention provides a prosthesis for use in treating ailments of the scaphoid. This prosthesis has a shape and size adapted to enable said prosthesis to replace at least a portion of the scaphoid and is made of a material having a Young's modulus approximately comprised between 10 and 35 GPa. The portion of the scaphoid to be replaced is typically a proximal portion thereof.

The material constituting the prosthesis is thus substantially equivalent to bone, from the viewpoint of elasticity and rubbing properties. Accordingly, the prosthesis according to the invention provides a high degree of comfort for the patient and avoids deterioration of the bones of the patient's wrist, while having a sufficient hardness to resist wear, even upon rubbing between the prosthesis and adjacent bone or cartilage.

Preferably, such material comprises pyrolytic carbon. Pyrolytic carbon has a low Young's modulus, comprised within the above-mentioned range, is hard-wearing and has significant elongation at rupture. It is also bio-compatible, chemically inert and stable over time. The crystalline structure of pyrolytic carbon is turbostratic and resists fracture. Further, pyrolytic carbon resists wear (especially when this takes the form of cyclic stresses) and, due to its low Young's modulus, does not wear away the bones in contact therewith. Another advantage of pyrolytic carbon resides in that it is isotropic, i.e. it has the same mechanical properties in three mutual orthogonal directions. Thus, the prosthesis according to the invention reacts identically with respect to the neighboring bones whatever the direction in which it is solicited.

If desired, the hard-wearing properties of the implant according to the invention can be further enhanced by allying the pyrolytic carbon with silicon carbide.

Preferably, the prosthesis according to the present invention has a polished external surface, in order to reduce friction between the prosthesis and the neighboring bones and more specifically between the prosthesis and neighboring cartilage. The prosthesis can thus slide smoothly on neighboring cartilage.

Preferably, the external surface of the prosthesis according to the invention comprises respective curved surface portions having different radii of curvature in at least two mutually orthogonal directions.

The shape of the prosthesis according to the present invention is particularly well adapted to ensure the mobility of the wrist without pain is maintained or recovered. More especially, implantation of the prosthesis according to the present invention enables the kinematics of the wrist to be preserved while keeping stability (perfect return to the initial position) because of the properties of the material used and the profile of the implant (the implant self-stabilizes without dislocation).

A prosthesis having the above-mentioned combination of size (replacement of a proximal portion of the scaphoid), shape (different radii of curvature in mutually orthogonal directions) and material (pyrolytic carbon), implanted in a patient's wrist, results in a joint with good mobility and stability, providing a high degree of comfort for the patient and durable over an extended period of time.

The radii of curvature of the implant according to the invention are suited to the anatomy of the wrist. More particularly, in preferred embodiments thereof, the implant comprises a first portion having a small radius of curvature (i.e. a highly-curved portion) corresponding to the conjugated profile of the scaphoid between the head of the capitate and the radius, and a second portion having a large radius of curvature (i.e. a flatter portion) corresponding to the profile of the scaphoid facing the radius. It has been found that, once implanted in the wrist, a prosthesis having such a shape provides especially natural movement of the wrist.

In the presently preferred embodiments of the invention, the implant is shaped so as to have different radii of curvature in three mutually orthogonal directions. It has been found that this feature greatly improves the stability of the implant against dislocation during movement. Typically, the implant has a substantially ellipsoidal shape.

The prosthesis of the present invention is particularly adapted to serve as a replacement for a proximal portion of the scaphoid. The size of the prosthesis can be varied so as to cater for different degrees of resection of the scaphoid. The desirable size of the prosthesis to use in a particular case can be determined according to a postero-anterior X-ray and a lateral wrist X-ray depending upon the amount of piston motion and the size of the volume to be filled, or by trying out color-coded sizers corresponding to different sizes of implant. It has been found to be preferable to use a slightly undersized prosthesis.

According to a further aspect thereof, the present invention provides a method of treatment of ailments of the scaphoid, the method consisting in the steps of surgically removing a first fragment of the scaphoid, leaving a second fragment thereof in situ, and implanting in place of the removed first fragment a prosthesis made of a material having a Young's modulus comprised approximately between 10 and 35 GPa. Typically, the first and second fragments correspond respectively to proximal and distal portions of the scaphoid.

Preferably, the material constituting the implanted prosthesis comprises pyrolytic carbon and the prosthesis has a polished external surface comprising respective curved surface portions having different radii of curvature in at least two mutually orthogonal directions.

The above-described method of treating scaphoid ailments results in recovery of maintenance of wrist mobility without pain. The surgical implant of the prosthesis maintains the cohesion of the first carpal row.

It is preferred that, in the above method, the implanted prosthesis should comprise a portion having a small radius of curvature (i.e. a highly-curved portion) corresponding to the conjugated profile of the scaphoid between the head of the capitate and the radius, and a portion having a large radius of curvature (i.e. a flatter portion) corresponding to the profile of the scaphoid facing the radius. As mentioned above, once implanted in the wrist, a prosthesis having such a shape provides especially free movement of the wrist.

Moreover, in the above method it is preferred to use a prosthesis having different radii of curvature in three mutually orthogonal directions and having for instance a substantially ellipsoidal shape. In this way, the risk of dislocation during subsequent movement of the wrist joint is minimized.

It is particularly advantageous to apply the treatment according to the present invention in case of scaphoid radial arthritis, pseudarthrosis (especially when affecting a small scaphoid fragment), avascular necrosis of a proximal scaphoid fragment or Preiser's disease, post-traumatic carpal instability with limited arthritis, or failures of surgical scaphoid fractures.

BRIEF DESCRIPTION OF THE DRAWINGS

FIG. 2 shows an implant according to a preferred embodiment of the present invention, wherein

FIGS. 3 to 7 are diagrams serving to illustrate an explanation of the derivation of the shape of the implants according to the present invention, wherein:

FIG. 3 is a diagram schematically representing the movement of bones in the wrist by a simple model consisting of three solids;

FIG. 4 is a diagram illustrating how, a the points of contact between the solids of the simple model of FIG. 3, the shapes of the solids can be approximated by circles;

FIG. 5 is a diagram illustrating a system of inner contact which can also be used to approximate the movement of the intermediate solid of the model of FIG. 3 relative to the fixed solid;

FIG. 6 is a diagram illustrating a system of inner contact which can also be used to approximate the movement of the upper solid of the model of FIG. 3 relative to the intermediate solid;

FIG. 7 is a diagram illustrating how the shape of the implants according to the present invention can be derived from the approximations of FIGS. 5 and 6;

DETAILED DESCRIPTION OF THE PREFERRED EMBODIMENTS

Preferred embodiments of implant according to the present invention will now be described with reference to FIGS. 2 to 9.

The implant 1 is an element preferably made of pyrolytic carbon and graphite, and having a particular shape. More specifically, the pyrolytic carbon is deposited on a graphite substrate in a conventional manner, so as to fully coat the graphite substrate and constitute the external surface of the implant. Pyrolytic carbon is an isotropic ceramic manufactured at temperatures of around 1400° C. The compatibility of pyrolytic carbon with tissues and blood has been demonstrated by its use, for over 20 years, for making replacement cardiac valves (over 1 million of such valves have been implanted). The techniques for fabrication of elements in pyrolytic carbon and graphite are well-known and so will not be described in detail here. Details can be found, for example, in U.S. Pat. No. 3,526,005.

Because of its turbostratic structure, pyrolytic carbon, even coated on a graphite element, presents a high resistance to fracture with a low modulus of elasticity (Young's modulus), of about 20 to 35 GPa, and a significant elongation before rupture. Also, the use of pyrolytic carbon enables the bones which are in contact with the prosthesis not to be worn out by rubbing with the latter.

The external surface of the implant 1 is polished, thereby reducing friction between the implant 1 and the neighboring cartilage and/or bone. The surface roughness R.A. is at most 0.1 μm and preferably 0.02 μm.

In order to render the implant radio-opaque, i.e. to permit monitoring of the implant 1 by radiography once the implant has been implanted into the patient's wrist, the graphic can advantageously be impregnated with tungsten.

In variant, the implant 1 is made of massive pyrolytic carbon, in which case no graphite is present in the implant.

In another variant, the implant 1 is realized by coating a substrate, such as a graphite substrate, with a diamond-like carbon using a plasma-assisted PVD (Physical Vapor Deposition) of a plasma-assisted CVD (Chemical Vapor Deposition).

In another variant, the implant 1 is realized by coating a graphite substrate with an appropriate bio-compatible plastic. Such a bio-compatible plastic is for example parylene.

Figure 1:
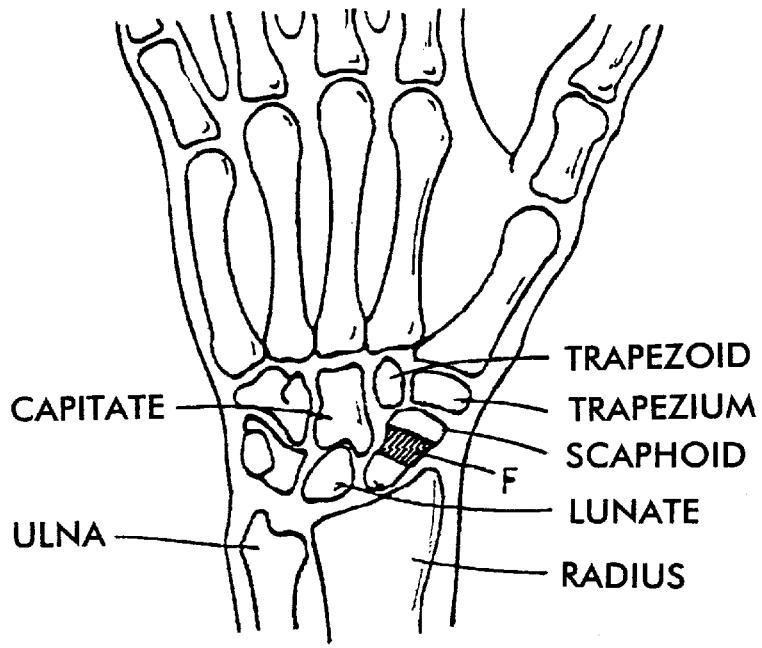
FIG. 1 is a diagram illustrating the principal bones of the human wrist (right hand, viewed looking at the palm)
Figure 2A:
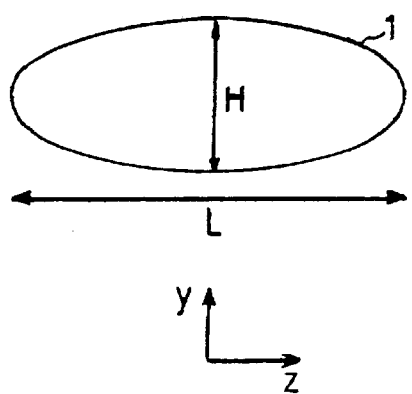
FIG. 2a is a side view.
Figure 2B:
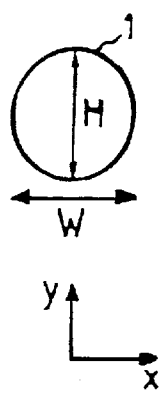
FIG. 2b is an end view of the implant.
Figure 2C:
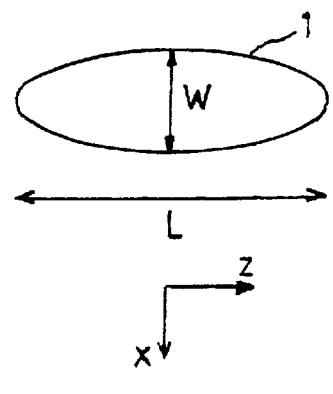
FIG. 2c is a top plan view of the implant.

The prosthesis 1 according to the present embodiment is generally oval in cross-section in each one of three mutually perpendicular planes respectively designated by (z, y), (x, y) and (z, x) in FIGS. 2a, 2b and 2c. Moreover, the length L, height H, and width W of the prosthesis are all different from one another. Preferably, the prosthesis has a substantially ellipsoidal shape, and in particular is approximately elliptic in cross-sectional shape in each of the planes (z, y), (x, y) and (z, x), that is, the cross-sectional shape in a given plane corresponds to the shape delimited by a pair of facing, intersecting arcs having the same radius of curvature, with the points of intersection of the arcs being rounded off. The appropriate values of the radii of curvature are related to the anatomy of the wrist, as is explained in greater detail below.

A statistical study of fractures of the scaphoid, conducted on both male and female patients, has enabled the determination of a set of "standard" prostheses according to the invention, suitable for treating the vast majority of ailments of the scaphoid. The dimensions of these "standard" prostheses are given in Table 1 below.

TABLE 1

|  | Length L (mm) | Width W (mm) | Height H (mm) |
| --- | --- | --- | --- |
| Example 1 | 18.9 | 9.5 | 10.6 |
| Example 2 | 17.9 | 8.5 | 9.6 |
| Example 3 | 17 | 7.5 | 8.6 |

Figure 8:
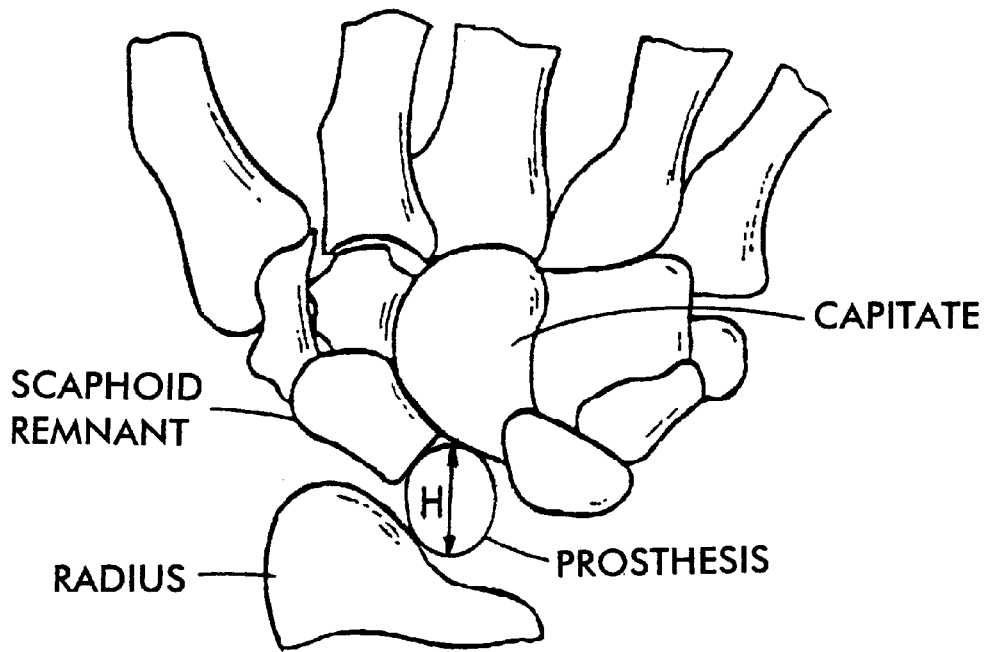
FIG. 8 is a diagram illustrating the orientation of a prosthesis according to the present invention when implanted in a wrist (viewed looking at the back of a right hand)
Figure 9:
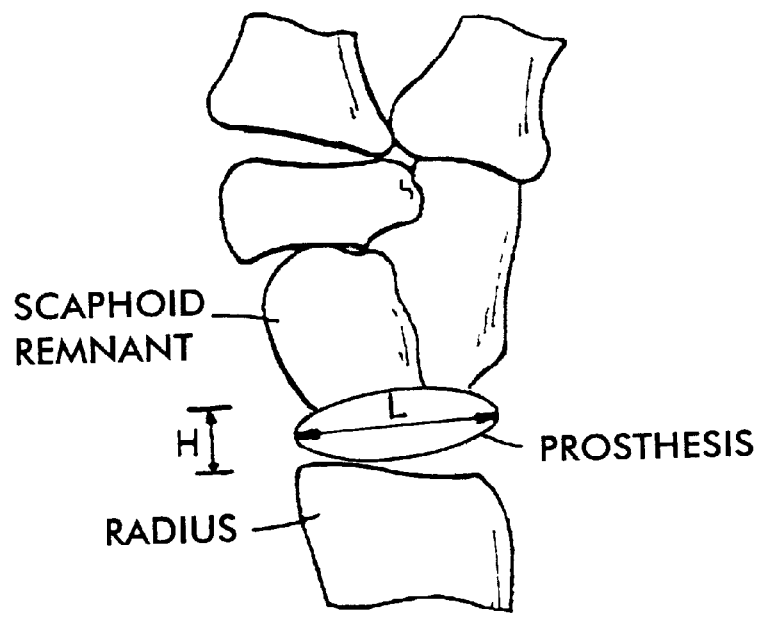
FIG. 9 is a diagram illustrating the orientation of a prosthesis according to the present invention when implanted in a wrist (viewed looking at the side of a right hand, the thumb facing forwards).

As mentioned above, the implant 1 is substantially ellipsoidal and has a first portion of large radius of curvature (relatively flat) which corresponds to the profile of the scaphoid facing the radius (see FIG. 9). It also has a second portion of small radius of curvature (relatively highly curved) which corresponds to the profile of the scaphoid between the head of the capitate and the radius (see FIG. 8). The width W of the implant 1 being smaller than the height H, leads to an increase in the curvature of the second portion and, thus, to an increase in ease of rolling of the prosthesis relative to the capitate and radius. Moreover, it has been found that the risk of dislocation of the wrist joint after implantation of the prosthesis is significantly reduced when $W \neq H$.

The shape of the implant according to the present invention was derived from a consideration of the kinematics of the bones in the wrist, based on certain models and approximations described below with reference to the diagrams of FIGS. 3 to 7.

Figure 3:
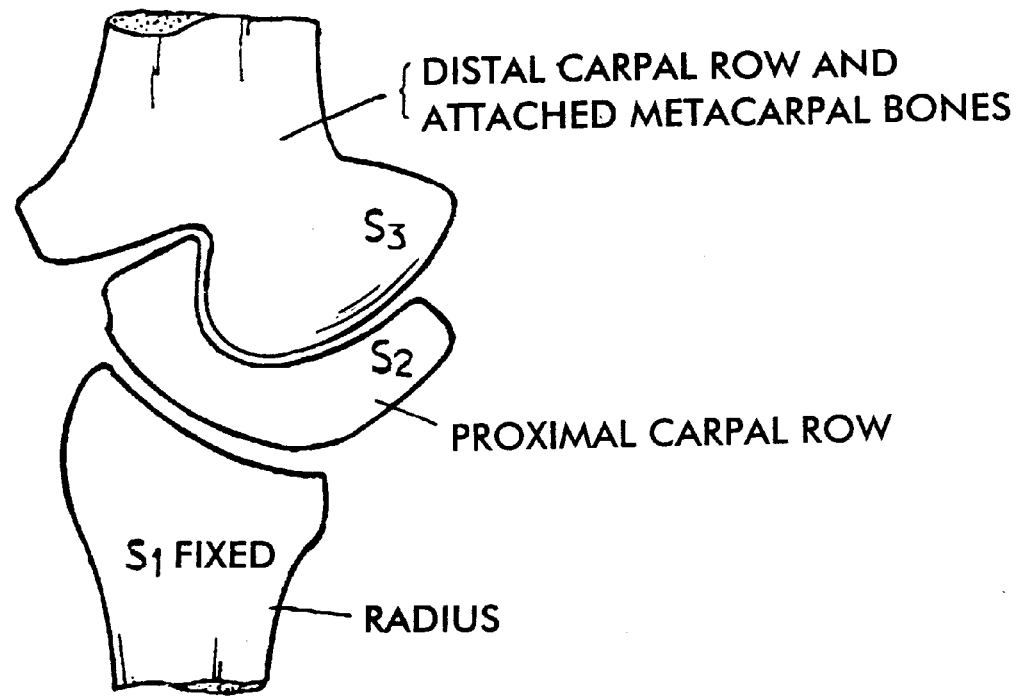

Movements of the wrist can be analyzed using a model treating the wrist as being composed of three solids S1, S2 and S3, roughly as illustrated in FIG. 3. The solid S1 corresponds to the radius and, thus, is considered to be fixed. The solid S2 corresponds to the bones of the first carpal row (scaphoid, lunate, triangular and pisiform bones), treated as a single entity. The solid S3 corresponds to the bones of the second carpal row (trapezium, trapezoid, capitate and hamate) treated as a single entity. Movements of the third solid S3 are considered to be caused by movement of the intermediate second solid S2, that is:

mDisplacement (S3 relative to S1)=Displacement (S2 relative to S1)+Displacement (S3 relative to S2).

The movement of the wrist are such that the three solids of the model of FIG. 3 experience only small displacements relative to one another. It thus becomes possible to reduce the analysis of movements of the wrist to an analysis of what happens at the points of contact between the different solids of the model of FIG. 3. At these points of contact, I, the shapes of the respective solids can be approximated using circles, as illustrated in FIG. 4.

Figure 4:
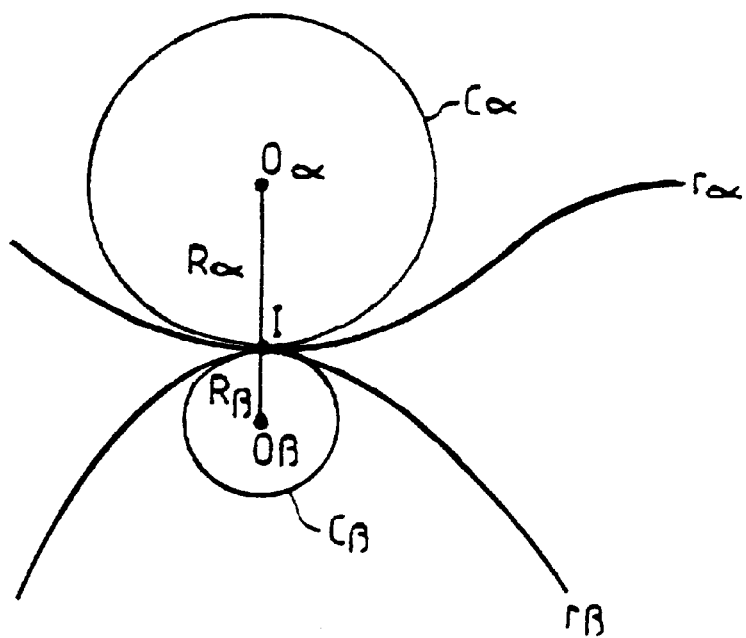

In FIG. 4, the curves $\Gamma_\alpha$ and $\Gamma_\beta$ represent the curved surfaces of solids which are in contact at a point I. At the point of contact, these surfaces can be represented by respective circles $C_\alpha$ and $C_\beta$, having centers $O_\alpha$ and $O_\beta$ and radii $R_\alpha$ and $R_\beta$.

Figure 5:
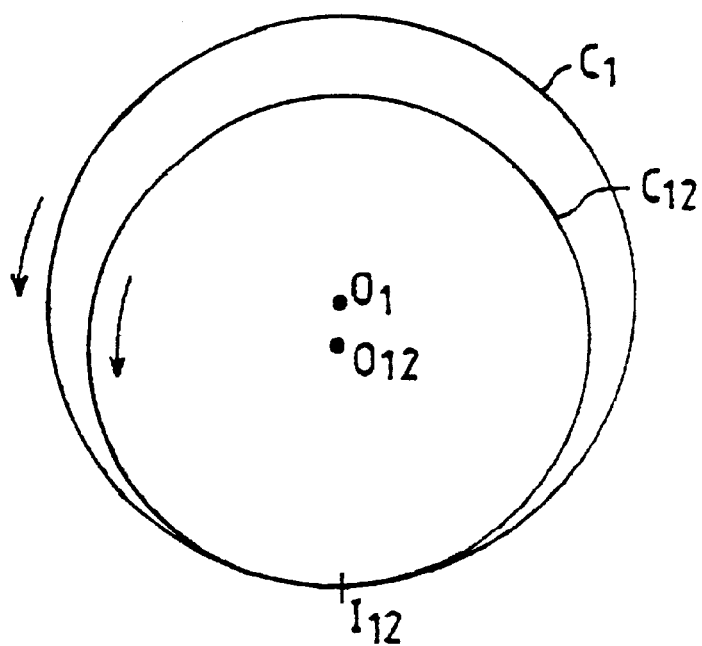

The movement of the intermediate and S2 relative to the fixed solid S1 can thus, be represented, as in FIG. 5, by a pair of nested circles C1 (representing the surface of the fixed solid S1 at the point of contact) and C12 (representing the portion of intermediate solid S2 at the point of contact with S1), the circle C12 rolling with respect to the circle C1.

Figure 6:
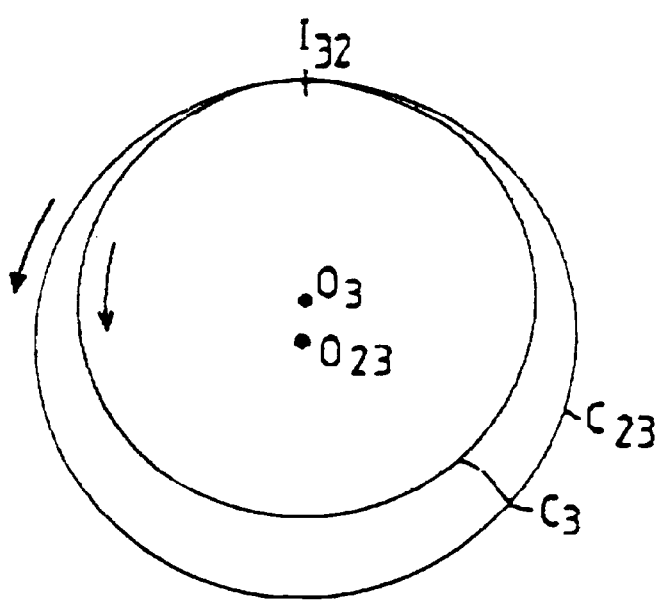

Now, when the wrist moves, the distal carpal row (modeled as solid S3) rotates in the same direction as the first carpal row (modeled as intermediate solid S2). In order for this to be possible, and for the angels of articulation between the various bones to be respected, it is necessary to consider that, on the model of FIG. 3, the solid S3 forms with the solid S2 a system resembling a mechanical gear with inner contact, as illustrated in FIG. 6. In FIG. 6, the movement of the solid S3 relative to the intermediate solid S2 is represented by a pair of nested circles C3 (representing the surface of solid S3 at the point of contact) and C23 (representing the portion of the intermediate solid S2 at the point of contact with S3), the circle C3 rolling with respect to the circle C23. This type of dynamic system results in rolling contact without slipping.

In order for the transmission of movement to solid S3 to be as effective as possible, it is necessary that the instantaneous contact between the various solids should take the form of a point contact (that is, the surfaces remain as tangent to one another as possible), and that slipping should be avoided. Such a situation will arise when the surfaces in contact are conjugated surfaces.

Figure 7:
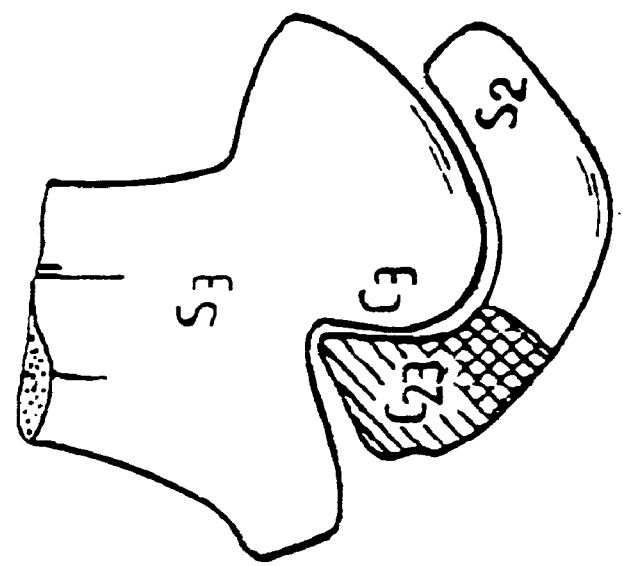
Figure 7:
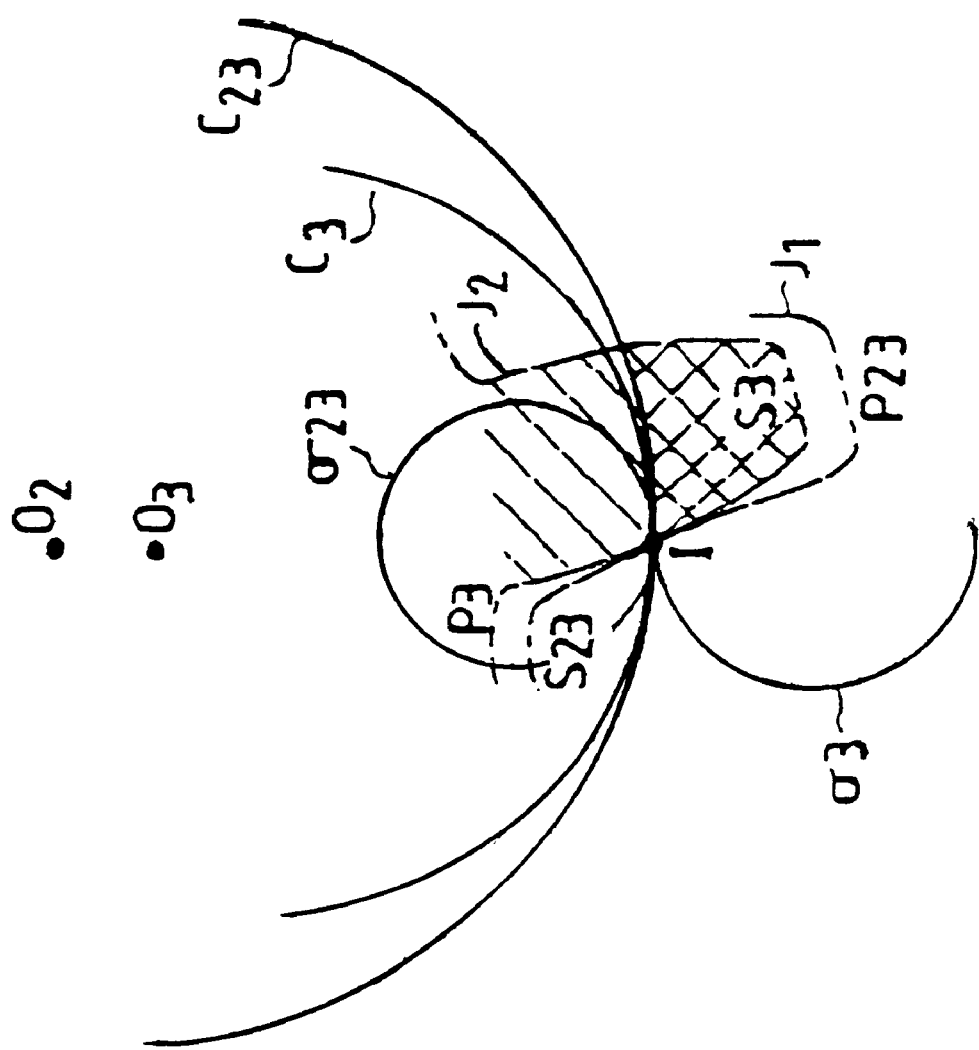

FIG. 7 shows the shape of conjugated surfaces, $J_1$, $J_2$ in a gear having internal contact and illustrating the analogy between the tenth of such a gear and the portion of the solid S2 which corresponds to the scaphoid. It can be considered that the hatched portions of the gear tooth and the solid S2 correspond to the scaphoid. The prosthesis of the present invention is designed to replace the portion of the scaphoid indicated by the cross-hatched portion of the solid S2. In practice, the surface of the radius facing this portion of the scaphoid is not smooth but bowed inwards, such that the prosthesis according to the invention can be considered to correspond to the extremity of the tooth represented by the surface $J_2$.

Accordingly, the prosthesis of the present invention is designed to have a portion having a large radius of curvature (i.e. a flatter portion) corresponding to the conjugated profile of the scaphoid facing the radius and, for similar reasons, to have a portion having a small radius of curvature (i.e. a highly-curved portion) corresponding to the conjugated profile of the scaphoid between the head of the capitate and the radius.

A preferred method of treating ailments of the scaphoid according to the present invention will now be described.

The preferred method of treatment consists in the surgical removal of a proximal scaphoid portion and the replacement thereof by an implant of the type described above. Before surgery, x-rays of the wrist are taken in order to determine the appropriate dimensions of the implant. More particularly, postero-anterior and lateral wrist x-rays are taken in order to evaluate the amount of piston motion required and the volume to be filled, the choice of implant dimensions being determined by the result of the evaluation, for example using overheads being of the same scale as the X-ray pictures and showing the outside profile of the prosthesis. The surgical procedure is then, as follow:

The approach is made dorsally, creating a Z-shaped incision in the skin along the extensor carpi radialis brevis and curving towards the thumb base in a proximo-distal fashion. Afterwards, the procedure uses a way between the radialis tendons or on the ulnar side of extensor carpi-radialis brevis. (The extensor pollicis longus is repaired and retracted because otherwise it interferes with this operation).

The capsule is incised longitudinally up to the capitate. It should be subperiosteum pushed towards the radial and ulnar sides on the lip of the radius.

The scaphoid fragment is removed, after sectioning the scapho-lunate ligament and excising the fibrous sinovium if necessary. If needed, an osteomy can be performed, in an oblique way, radial to ulnar side, on the retained distal scaphoid fragment. It has been found in some cases that the radial styloidprocess can be removed without compromising in any way the stability of the implant. The capitate is not shaped but left convex. If the scaphoid surface of the distal radius has arthrosic signs then it is appropriate to create Pridies perforations on the radial fossa using a 1/10 broach.

At this stage, the prosthesis of chosen dimensions can be put into place. As indicated above, the portion of the implant having a small radius of curvature (i.e. a highly-curved portion) corresponding to the conjugated profile of the scaphoid between the head of the capitate and the radius is disposed facing those bones (see FIG. 8), whereas the portion of the implant having a large radius of curvature (i.e. a flatter portion) corresponding to the profile of the scaphoid facing the radius is disposed facing the upper side of the radius (the radius being oriented as shown in FIG. 9).

FIG. 8 and 9 illustrate the disposition of the prosthesis in the wrist of a right hand. FIG. 8 represents a view looking at the back of a right hand and FIG. 9 represents a view looking at the side of the right hand, the thumb facing forwards.

Preferably, the stability of implant positioning under movements of flexion-extension and lateral bending of the wrist is checked, even while the capsule is still open.

As a matter of routine, the capsular closure is loose, performed longitudinally using two or three points in X. The extensor radialis tendons will reposition on the capsular opening and especially stabilize the dorsal gap in flexion and in dynamic way. The extensor retinaculum incised or excised distally is not reconstituted.

The skin closure is done on a suction drain. The day after the surgical procedure has been performed, the wrist should be immobilized in a neutral position in a short arm cast. This cast should be left in place for two to three weeks. After this time, the rehabilitation can start using a removable splint. This splint is to be worn in an intermittent fashion for about one month. Use of a removable splint (no arm east) can sometimes lead to early rehabilitation. However, no acceleration of the recovery process is seen and mobility results are identical.

As an alternative embodiment of the method according to the invention, the choice of the dimensions of the prosthesis to be implanted into the patient's wrist is performed using color coded sizers having the same shape as that of the implant 1. Each color coded sizer consists of an element having a particular size and a corresponding color. Several color-coded sizers are successively inserted into the patient wrist. The particular size of the color coded sizer that is best adapted to the patient's wrist corresponds to the size of the prosthesis to be implanted.

It should be noted that the above-described method of treatment is contra-indicated in certain cases, notably in cases of infection or systemic disease, advanced deformity of the distal portion of the radius, SLAC wrist, advanced silicone synovitis of the wrist bone, irreparable conditions of the tendon system or inadequate soft tissue support.

What is claimed is:

1. A prosthesis for use in the treatment of ailments of the scaphoid, having a shape and size adapted to enable said prosthesis to replace at least a portion of the scaphoid while a distal portion of the scaphoid remains in place, wherein said prosthesis is made of a material having a Young's modulus approximately comprised between 10 and 35 GPa.

2. A prosthesis according to claim 1, having an external surface comprising respective curved surface portions having different radii of curvature in at least two mutually orthogonal directions.

3. A prosthesis according to claim 2, wherein said respective portions having different radii of curvature comprise:

a first portion having a small radius of curvature corresponding to the conjugated profile of the scaphoid between the head of the capitate and the radius; and a second portion having a large radius of curvature corresponding to the profile of the scaphoid facing the radius.

4. A prosthesis according to claim 2, wherein said external surface comprises respective curved surface portions having different radii of curvature in three mutually orthogonal directions.

5. A prosthesis according to claim 4, wherein the dimensions thereof in each of said three mutually orthogonal directions are different from one another.

6. A prosthesis according to claim 1, having a substantially ellipsoidal shape.

7. A prosthesis for use in the treatment of ailments of the scaphoid, having a shape and size adapted to enable said prosthesis to replace at least a portion of the scaphoid while a distal portion of the scaphoid remains in place, wherein said prosthesis is made of a material comprising pyrolytic carbon.

8. A prosthesis according to claim 7, wherein said pyrolytic carbon forms at least an external surface of said prosthesis.

9. A prosthesis according to claim 7, wherein said material further comprises graphite, and graphite being coated with said pyrolytic carbon.

10. A prosthesis according to claim 9, wherein said graphite is impregnated with tungsten.

11. A prosthesis according to claim 7, having an external surface comprising respective curved surface portions having different radii of curvature in at least two mutually orthogonal directions.

12. A prosthesis according to claim 11, wherein said respective portions having different radii of curvature comprise:

a first portion having a small radius of curvature corresponding to the conjugated profile of the scaphoid between the head of the capitate and the radius; and a second portion having a large radius of curvature corresponding to the profile of the scaphoid facing the radius.

13. A prosthesis according to claim 11, wherein said external surface comprises respective curved surface portions having different radii of curvature in three mutually orthogonal directions.

14. A prosthesis according to claim 13, wherein the dimensions thereof in each of said three mutually orthogonal directions are different from one another.

15. A prosthesis according to claim 7, having a substantially ellipsoidal shape.

16. A prosthesis according to claim 1, having a shape and size adapted to enable said prosthesis to be placed adjacent to the radius, the capitate, the lunate and a distal portion of the scaphoid.

17. A prosthesis according to claim 1, wherein said prosthesis is adapted to be in a rubbing relationship with any bone contacting said prosthesis when said prosthesis is implanted in a patient's wrist.

18. A prosthesis according to claim 7, having a shape and size adapted to enable said prosthesis to be placed adjacent to the radius, the capitate, the lunate and a distal portion of the scaphoid.

19. A prosthesis according to claim 7, wherein said prosthesis is adapted to be in a rubbing relationship with any bone contacting said prosthesis when said prosthesis is implanted in a patient's wrist.

20. A prosthesis according to claim 1 having a polished external surface, such that said prosthesis can smoothly slide on the bones neighboring said prosthesis when said prosthesis is implanted in a patient's wrist.

21. A prosthesis according to claim 7 having a polished external surface, such that said prosthesis can smoothly slide on the bones neighboring said prosthesis when said prosthesis is implanted in a patient's wrist.

* * * * *